United States Patent
Akagane

(10) Patent No.: US 11,602,770 B2
(45) Date of Patent: Mar. 14, 2023

(54) VIBRATION TRANSMITTING MEMBER AND ULTRASONIC TREATMENT INSTRUMENT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1286 days.

(21) Appl. No.: 16/029,151

(22) Filed: Jul. 6, 2018

(65) Prior Publication Data

US 2018/0311703 A1     Nov. 1, 2018

Related U.S. Application Data

(63) Continuation of application No. PCT/JP2016/050340, filed on Jan. 7, 2016.

(51) Int. Cl.
*B06B 1/06* (2006.01)
*B06B 3/00* (2006.01)
(Continued)

(52) U.S. Cl.
CPC ........ *B06B 1/06* (2013.01); *A61B 17/320092* (2013.01); *A61B 18/00* (2013.01);
(Continued)

(58) Field of Classification Search
CPC ... A61B 17/320092; A61B 18/00; B06B 3/00; B06B 1/06; A16B 2017/320094;
(Continued)

(56) References Cited

U.S. PATENT DOCUMENTS 5,001,649 A * 3/1991 Lo .................... B06B 1/0253
                                                     331/181
5,104,593 A * 4/1992 Joseph .................. G05D 5/03
                                                     700/196
(Continued)

FOREIGN PATENT DOCUMENTS

JP     H09-038099  A      2/1997
JP     H0938099    *      2/1997  ............. A61B 17/32
(Continued)

OTHER PUBLICATIONS

Jul. 24, 2019 Office Action issued in Chinese Patent Application No. 201680078286.2.
(Continued)

*Primary Examiner* — Clayton E. LaBalle
*Assistant Examiner* — Kevin C Butler
(74) *Attorney, Agent, or Firm* — Oliff PLC

(57) ABSTRACT

Each of segments of a vibration transmitting member has a dimension of a half-wave length between mutually neighboring vibration anti-nodes and sets a vibration node as a center. In each of recess segments included in the segments, the vibration node is located in a groove, and an intermediate extension extends from a proximal end to a distal end in the groove in a longitudinal direction. At least two of the recess segments are different from each other with respect to at least one of a dimension in the longitudinal direction of the intermediate extension and a cross-sectional area perpendicular to the longitudinal direction of the intermediate extension.

14 Claims, 4 Drawing Sheets

(51) Int. Cl.
*A61B 18/00* (2006.01)
*A61B 17/32* (2006.01)
*A61B 17/00* (2006.01)
*A61B 17/22* (2006.01)

(52) U.S. Cl.
CPC ...... *B06B 3/00* (2013.01); *A61B 2017/00473* (2013.01); *A61B 2017/22018* (2013.01); *A61B 2017/320088* (2013.01); *A61B 2017/320094* (2017.08)

(58) Field of Classification Search
CPC ........... A16B 2017/00473; A16B 2017/22018; A16B 2017/320088; A16B 17/320092
USPC .......................................................... 310/348
See application file for complete search history.

(56) References Cited

U.S. PATENT DOCUMENTS

| | | | | |
|---|---|---|---|---|
| 5,269,297 | A * | 12/1993 | Weng | A61B 17/22012 606/128 |
| 5,516,043 | A * | 5/1996 | Manna | B05B 17/0623 239/548 |
| 5,989,275 | A * | 11/1999 | Estabrook | A61B 17/22012 606/169 |
| 8,226,675 | B2 * | 7/2012 | Houser | A61B 17/320068 606/169 |
| 8,798,950 | B2 * | 8/2014 | Nikolic | B06B 1/0253 310/317 |
| 8,836,200 | B2 * | 9/2014 | Young | B06B 3/00 310/323.02 |
| 2003/0135136 | A1 | 7/2003 | Murakami | |
| 2005/0187514 | A1 * | 8/2005 | Rabiner | A61B 17/22012 604/22 |
| 2010/0286791 | A1 * | 11/2010 | Goldsmith | A61B 17/12022 604/524 |
| 2014/0163664 | A1 * | 6/2014 | Goldsmith | A61B 17/0057 604/93.01 |
| 2014/0309562 | A1 | 10/2014 | Ito | |
| 2017/0020777 | A1 * | 1/2017 | Yamada | B06B 1/0644 |
| 2021/0145445 | A9 * | 5/2021 | Goldsmith | A61B 17/3468 |

FOREIGN PATENT DOCUMENTS

| | | | | |
|---|---|---|---|---|
| JP | 2000-509637 A | | 8/2000 | |
| JP | 2002-65688 A | | 3/2002 | |
| JP | 2005-103015 A | | 4/2005 | |
| WO | WO-2016047241 A1 * | | 3/2016 | ........... B06B 1/0644 |
| WO | WO-2017119099 A1 * | | 7/2017 | ...... A61B 17/320092 |
| WO | WO-2018070043 A1 * | | 4/2018 | ...... A61B 17/320068 |

OTHER PUBLICATIONS

Jul. 30, 2019 Extended Search Report issued in European Patent Application No. 16883602.1.
Mar. 15, 2016 International Search Report issued in Interntional Patent Application PCT/JP2016/050340.
Jul. 10, 2018 International Preliminary Report on Patentability issued in International Patent Application PCT/JP2016/050340.

* cited by examiner

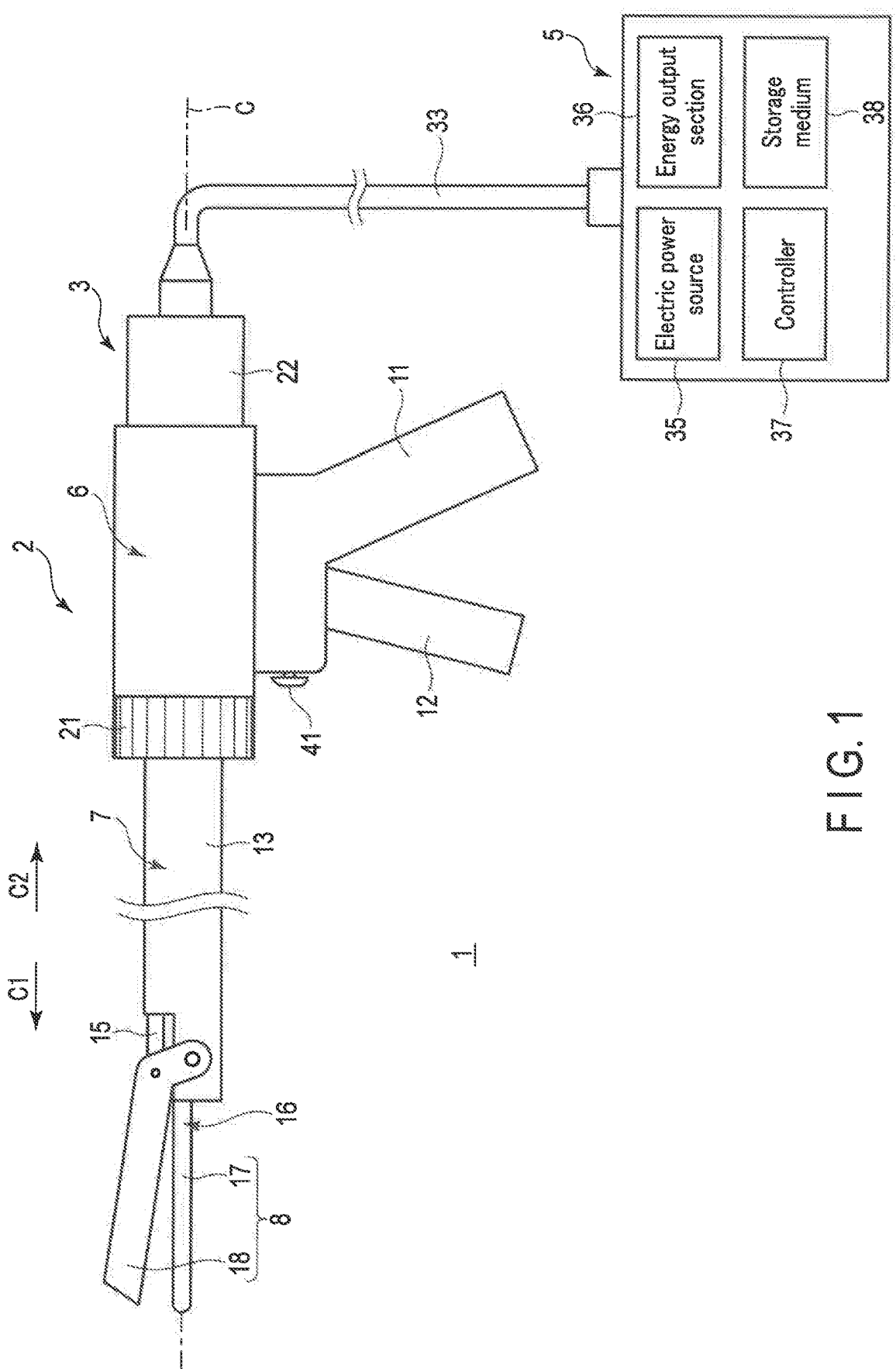
F I G. 1

VIBRATION TRANSMITTING MEMBER AND ULTRASONIC TREATMENT INSTRUMENT

CROSS-REFERENCE TO RELATED APPLICATIONS

This is a Continuation Application of PCT Application No. PCT/JP2016/050340, filed Jan. 7, 2016, the entire contents of which are incorporated herein by reference.

BACKGROUND OF THE INVENTION

1. Field of the Invention

The present invention relates to a vibration transmitting member which transmits ultrasonic vibration. The invention also relates to an ultrasonic treatment instrument and a vibrating body unit, each including the vibration transmitting member.

2. Description of the Related Art

Jpn. Pat. Appln. KOKAI Publication No. 2002-65688 discloses an ultrasonic treatment instrument including a vibration transmitting member which transmits ultrasonic vibration, the ultrasonic vibration being generated by an ultrasonic transducer. In this ultrasonic treatment instrument, an energy applying portion is formed in a distal portion of the vibration transmitting member. The ultrasonic vibration transmitted through the vibration transmitting member is applied from the energy applying portion to a treated target which is grasped between the energy applying portion and a grasping member.

BRIEF SUMMARY OF THE INVENTION

According to one aspect of the invention, a vibration transmitting member including: an attached portion to which an ultrasonic transducer is attached, the ultrasonic transducer being configured to vibrate the vibration transmitting member at a predetermined resonance frequency by transmitting ultrasonic vibration; and a plurality of segments which are disposed in a longitudinal direction, wherein each of the segments has a dimension of a half-wave length between mutually neighboring vibration anti-nodes and sets a vibration node as a center, in a state in which the vibration transmitting member vibrates at the predetermined resonance frequency, at least two of the segments are recess segments, each of the recess segments being configured such that a groove recessed toward an inter peripheral side is formed in a portion in which the vibration node is located, each of the recess segments includes a proximal-side extension extending from a proximal end of the half-wave length to a proximal end of the groove in the longitudinal direction, a distal-side extension extending from a distal end of the groove to a distal end of the half-wave length in the longitudinal direction, and an intermediate extension extending from the proximal end of the groove to the distal end of the groove in the longitudinal direction, the proximal-side extension and the distal-side extension, in each of the recess segments, have an identical dimension in the longitudinal direction and an identical cross-sectional area perpendicular to the longitudinal direction relative to each other, and at least two of the recess segments are different from each other with respect to at least one of a dimension in the longitudinal direction of the intermediate extension and a cross-sectional area perpendicular to the longitudinal direction of the intermediate extension.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating a treatment system according to a first embodiment;

DETAILED DESCRIPTION OF THE INVENTION

First Embodiment

Figure 2:
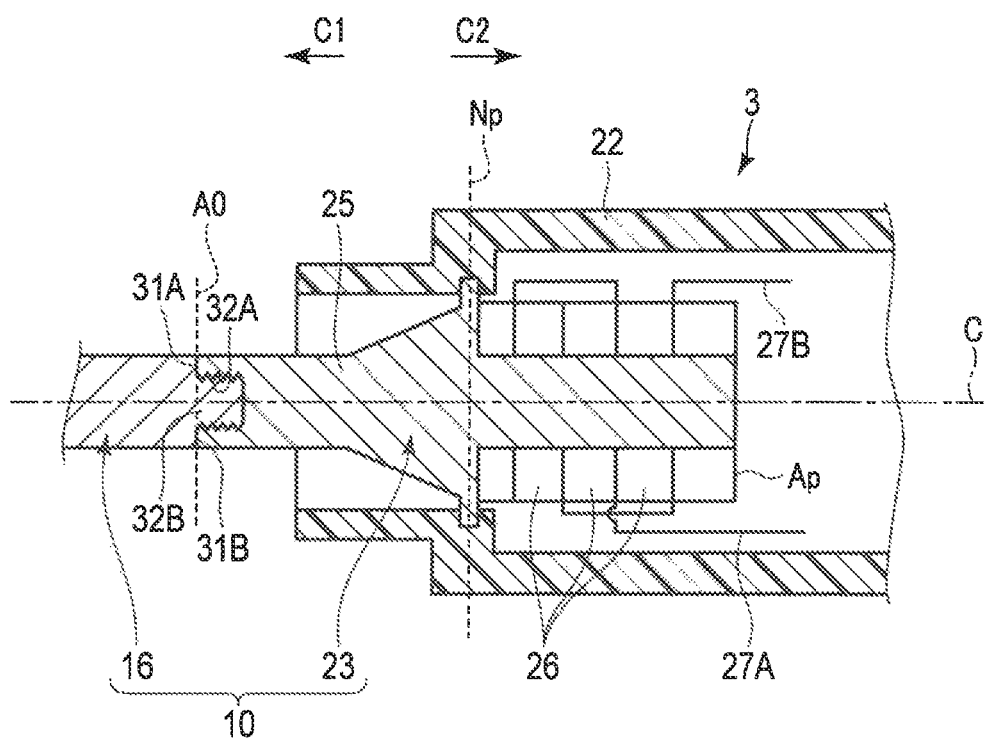
FIG. 2 is a cross-sectional view schematically illustrating the configuration of a transducer unit according to the first embodiment.

A first embodiment of the present invention is described with reference to FIG. 1 to FIG. 4. FIG. 1 is a view illustrating a treatment system 1 of the present embodiment. As illustrated in FIG. 1, the treatment system 1 includes an ultrasonic treatment instrument 2, a transducer unit 3 and an energy control device 5. The ultrasonic treatment instrument 2 has a longitudinal axis C. Here, a direction along the longitudinal axis C is defined as a longitudinal direction (directions indicated by arrow C1 and arrow C2). In addition, one side of the longitudinal direction is a distal side (arrow C1 side), and an opposite side to the distal side is a proximal side (arrow C2 side).

The ultrasonic treatment instrument 2 includes a housing 6 which can be held, a shaft portion (shaft) 7 which is coupled to the housing 6 from the distal side, and an end effector 8 provided in a distal portion of the shaft portion 7. The housing 6 includes a grip (stationary handle) 11 which extends along a direction crossing the longitudinal axis C. In addition, a handle (movable handle) 12 is rotatably attached to the housing 6. By the handle 12 rotating relative to the housing 6, the handle 12 opens or closes relative to the grip 11.

The shaft portion 7 includes a cylindrical sheath 13 which forms an exterior, and a movable portion (movable member) 15 which extends in the inside of the sheath 13. Each of the sheath 13 and movable portion 15 extends along the longitudinal axis C (longitudinal direction). For example, the center axis of the sheath 13 is substantially coaxial with the longitudinal axis C. In the inside of the housing 6, the handle 12 is coupled to a proximal portion of the movable portion 15. By the handle 12 opening or closing relative to the grip 11, the movable portion 15 moves relative to the housing 6 and sheath 13 in the longitudinal direction (along the longitudinal axis C).

A vibration transmitting member (ultrasonic probe) 16 extends from the inside of the housing 6 toward the distal side. The vibration transmitting member 16 is formed of a material with high vibration transmissibility such as Ti-6Al-4V or duralumin. In addition, the vibration transmitting member 16 is inserted through the shaft portion 7, and extends along the longitudinal axis C through the inside of the shaft portion 7 (sheath 13 and movable portion 15). An energy applying portion (probe treatment section) 17 is formed in a distal portion of the vibration transmitting member 16. The energy applying portion (first grasping piece) 17 projects from the distal end of the shaft portion 7 toward the distal side.

A grasping member (jaw) 18 is rotatably attached to a distal portion of the sheath 13. In addition, a distal portion of the movable portion (movable pipe) 15 is connected to the grasping member (second grasping piece) 18. By the movable portion 15 moving along the longitudinal axis C in accordance with the movement of the handle 12, the grasping member 18 rotates, and the energy applying portion (energy applier) 17 and grasping member 18 open or close relative to each other. In the present embodiment, the end effector 8 is composed of the energy applying portion 17 and grasping member 18. By the energy applying portion 17 and grasping member 18 closing relative to each other, a treated target such as a biological tissue can be grasped between the energy applying portion 17 and grasping member 18.

In addition, a rotation knob 21 is attached to the housing 6, and the rotation knob 21 is fixed to the sheath 13. By rotating the sheath 13 around the longitudinal axis C relative to the housing 6, the shaft portion 7, end effector 8 and vibration transmitting member 16 rotate together around the longitudinal axis C relative to the housing 6.

The transducer unit 3 is coupled to the housing 6 from the proximal side. FIG. 2 is a view illustrating the configuration of the transducer unit 3. As illustrated in FIG. 1 and FIG. 2, the transducer unit 3 includes a transducer case 22, and an ultrasonic transducer 23 which is disposed in the inside of the transducer case 22. In the inside of the housing 6, the transducer case 22 is attached to the shaft portion 7 from the proximal side. The ultrasonic transducer 23 includes a relay member 25, piezoelectric elements 26 (four piezoelectric elements 26 in this embodiment) which are attached to the relay member 25, and electrode members 27A and 27B which are attached to the relay member 25. Each of the piezoelectric elements 26 is interposed between the electrode members 27A and 27B.

In the inside of the housing 6, the relay member 25 is connected to the vibration transmitting member 16 from the proximal side, and the ultrasonic transducer 23 is attached to the vibration transmitting member 16 from the proximal side. Thereby, a vibrating body unit 10 is formed by the vibration transmitting member 16 and ultrasonic transducer 23. In this embodiment, in the vibrating body unit 10, in the state in which the ultrasonic transducer 23 is attached to the vibration transmitting member 16, an abutment surface 31B of the vibration transmitting member 16 abuts on a distal surface 31A of the ultrasonic transducer 23 (relay member 25). In addition, in this embodiment, in the ultrasonic transducer 23, an engaging groove 32A, which is recessed toward the proximal side from the distal surface 31A, is formed. In the vibration transmitting member 16, an engaging projection 32B, which projects toward the proximal side from the abutment surface 31B, is formed. By the engaging projection 32B being engaged in the engaging groove 32A, the vibration transmitting member 16 is connected to the ultrasonic transducer 23.

One end of a cable 33 is connected to the transducer unit 3, and the other end of the cable 33 is detachably connected to the energy control device 5. The energy control device 5 includes an electric power source 35 such as a battery or a plug socket, an energy output section (energy output source) 36 including a converter circuit, etc., a controller 37 such as a processor or an integrated circuit including a CPU (Central Processing Unit) or an ASIC (application specific integrated circuit), and a storage medium 38. The energy output section 36 is electrically connected to the ultrasonic transducer 23 via electric wiring (not shown) or the like provided in the inside of the cable 33. In addition, an operation button 41 functioning as an energy operation input portion (operation input member) is attached to the housing 6. In the treatment system 1, for example, a signal path (not shown) is formed through the inside of the transducer unit 3 and cable 33. Based on operation signals, etc., which are transmitted through the signal path, the controller 37 judges whether an operation input is being performed by the operation button 41 or not.

Based on the detection of an operation input by the operation button 41, the controller 37 drives the energy output section 36. Thereby, the energy output section 36 converts electric power from the electric power source 35 to, for example, AC electric power of a predetermined frequency, and outputs the converted electric energy. Then, by the electric energy being supplied from the energy output section 36 to the ultrasonic transducer 23, a voltage (e.g. an AC voltage of a predetermined frequency) is applied between the electrode members 27A and 27B. Thereby, each of the piezoelectric elements 26 converts the current (e.g. an AC current of a predetermined frequency) to ultrasonic vibration, and ultrasonic vibration is generated by the ultrasonic transducer 23.

The ultrasonic vibration generated by the ultrasonic transducer 23 is transmitted to the vibration transmitting member 16 through the distal surface 31A of the ultrasonic transducer 23 and the abutment surface 31B of the vibration transmitting member 16. Then, in the vibration transmitting member 16, the ultrasonic vibration is transmitted to the energy applying portion 17 from the proximal side toward the distal side. The energy applying portion 17 applies the transmitted ultrasonic vibration to a treated target grasped between the energy applying portion 17 and grasping member 18, thereby treating the treated target by using the ultrasonic vibration. In this embodiment, by the vibration transmitting member 16 transmitting the ultrasonic vibration, the vibrating body unit 10 including the vibration transmitting member 16 vibrates (resonates) at a predetermined resonance frequency (e.g. 47 kHz). At this time, the vibrating body unit 10 performs longitudinal vibration having a vibration direction which is substantially parallel to the longitudinal direction (longitudinal axis C).

Figure 3:
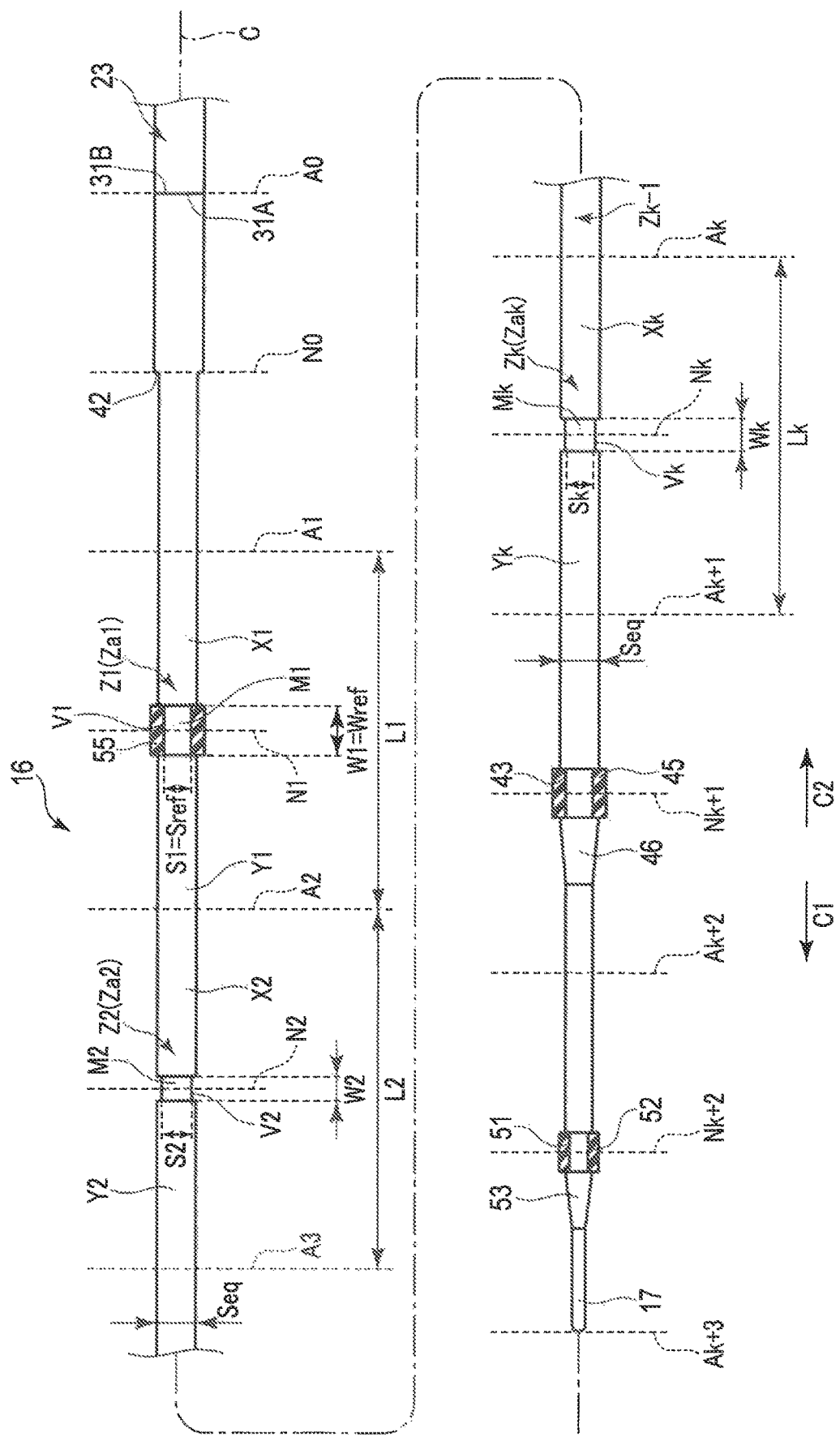
FIG. 3 is a schematic view illustrating the configuration of a vibration transmitting member according to the first embodiment.

FIG. 3 is a view illustrating the configuration of the vibration transmitting member 16. As illustrated in FIG. 2 and FIG. 3, in this embodiment, the vibrating body unit 10 vibrates at a predetermined resonance frequency. Thereby, in the ultrasonic transducer 23, a vibration anti-node Ap and a vibration node Np occur. In the vibration transmitting member, a plurality of vibration anti-nodes Ai (i=0, 1, . . . , k, k+1, k+2, k+3) and a plurality of vibration nodes Nj (j=0, 1, . . . , k, k+1, k+2) occur. At this time, the vibration anti-node Ap is located at the proximal end of the ultrasonic transducer 23 (the proximal end of the vibrating body unit 10), and a vibration anti-node A0 is located in a connection position (abutment surface 31B) between the ultrasonic transducer 23 and vibration transmitting member 16. In addition, a range between the vibration anti-node Ap and vibration anti-node A0 corresponds to a half-wave length of vibration at the predetermined resonance frequency, and the vibration node Np occurs between the vibration anti-node Ap and vibration anti-node A0.

Besides, it is assumed that, among the vibration anti-nodes Ai occurring in the vibration transmitting member 16, the vibration anti-node A0 is located most proximally, and a vibration anti-node Ak+3 is located most distally. A natural number i of the vibration anti-node Ai increases one by one toward the distal side. Similarly, it is assumed that, among the vibration nodes Nj occurring in the vibration transmitting member 16, a vibration node N0 is located most proximally, and a vibration node Nk+2 is located most distally. A natural number j of the vibration node Nj increases one by one toward the distal side. In addition, each of the vibration nodes Nj occurs in a half-wave length portion between a vibration anti-node (corresponding Aj) and a vibration anti-node (corresponding Aj+1). In the state in which the vibration transmitting member 16 vibrates at the predetermined resonance frequency, the vibration anti-node Ak+3 is located at the distal end of the vibration transmitting member 16 (the distal end of the vibrating body unit 10).

In the vibration transmitting member 16, for example, a step horn (amplitude increasing portion) 42 is formed as a part which increases an amplitude. The step horn 42 is provided on the distal side with respect to the abutment surface 31B. In the step horn 42, a cross-sectional area, which is substantially perpendicular to the longitudinal axis C, decreases from the proximal side toward the distal side. In the state in which the vibrating body unit 10 (vibration transmitting member 16) vibrates at the predetermined resonance frequency, the vibration node N0 is located in the step horn 42. Since each of the vibration anti-nodes Ai is located apart from the step horn 42, the amplitude of ultrasonic vibration is increased in the step horn 42. Note that since the step horn 42 is provided in the half-wave length portion between the vibration anti-node A0 and vibration anti-node A1 of the vibration at the predetermined resonance frequency, this portion has an asymmetric shape in the longitudinal direction with respect to the vibration node N0 as the center. In the half-wave length portion between the vibration anti-node A0 and vibration anti-node A1, the cross-sectional area perpendicular to the longitudinal axis C of the vibration transmitting member 16 becomes constant at Seq in a part which is located on the distal side with respect to the step horn 42.

In addition, in the vibration transmitting member 16, grooves 43 and 51, which are recessed toward the inner peripheral side, and horns (amplitude increasing portions) 46 and 53 are formed. Each of the grooves 43 and 51 is formed over the entire circumference around the longitudinal axis C. An annular liner member 45 is attached to the groove 43 from the outer peripheral side, and an annular liner member 52 is attached to the groove 51 from the outer peripheral side. Each of the liner members 45 and 52 is formed of, for example, an elastic material such as rubber, which has electrical insulativeness and heat resistance, and is engaged with the corresponding groove (corresponding one of 43 and 51). Besides, the movable portion 15 of the shaft portion 7 abuts on the liner member 45 from the outer peripheral side, and the sheath 13 of the shaft portion 7 abuts on the liner member 52 from the outer peripheral side. The horn 46 extends from the distal end of the groove 43 toward the distal side, and the horn 53 extends from the distal end of the groove 51 toward the distal side. In each of the horns 46 and 53, the cross-sectional area substantially perpendicular to the longitudinal axis C decreases from the proximal side toward the distal side. Furthermore, the distal end of the horn 53 is continuous with the energy applying portion 17.

In the state in which the vibrating body unit 10 (vibration transmitting member 16) vibrates at the predetermined resonance frequency, a vibration node Nk+1 is located in the groove 43, and a vibration node Nk+2 is located in the groove 51. Thus, the transmission of ultrasonic vibration from the vibration transmitting member 16 to the shaft portion 7 through the liner members 45 and 52 is prevented. Besides, in the state in which the vibrating body unit 10 vibrates at the predetermined resonance frequency, a vibration anti-node Ak+2 is located on the distal side with respect to the distal end of the horn 46, and a vibration anti-node Ak+3 is located on the distal side with respect to the distal end of the horn 53. Since each vibration anti-node Ai is located apart from the horn 46, 53, the amplitude of ultrasonic vibration is increased in each of the horns 46 and 53. Note that since the horn 46 is provided in the half-wave length portion between the vibration anti-node Ak+1 and vibration anti-node Ak+2 of the vibration at the predetermined resonance frequency, this portion has an asymmetric shape in the longitudinal direction with respect to the vibration node Nk+1 as the center. Similarly, since the horn 53 is provided in the half-wave length portion between the vibration anti-node Ak+2 and vibration anti-node Ak+3 of the vibration at the predetermined resonance frequency, this portion has an asymmetric shape in the longitudinal direction with respect to the vibration node Nk+2 as the center. In the half-wave length portion between the vibration anti-node Ak+1 and vibration anti-node Ak+2, the cross-sectional area perpendicular to the longitudinal axis C of the vibration transmitting member 16 becomes Seq in a part which is located on the proximal side with respect to the groove 43.

In the vibration transmitting member 16, a plurality of segments Zm (m=1, 2, ..., k) extend. The segments Zm are provided between the step horn 42 and groove 43 in the longitudinal direction, and extend in mutually different regions in the longitudinal direction. Among the segments Zm, a segment Z1 is located most proximally, and a segment Zk is located most distally. A natural number m of the segments Zm increases one by one toward the distal side. The distal end of each of the segments Zm, except the segment Zk, is continuous with the proximal end of the segment Zm+1. For example, the distal end of the segment Z1 is continuous with the proximal end of the segment Z2, and the distal end of the segment Zk−1 is continuous with the proximal end of the segment Zk. Note that the segments Zm are not mutually separate members, and all segments Zm are formed in the vibration transmitting member 16 that is a single member. Thus, the segments Zm have mutually substantially uniform physicality such as Young's modulus E.

In the state in which the vibrating body unit 10 vibrates at the predetermined resonance frequency, each of the segments Zm corresponds to a half-wave length portion between two mutually neighboring, corresponding vibration anti-nodes (corresponding Am and Am+1). For example, the segment Z1 corresponds to a half-wave length portion between the mutually neighboring vibration anti-nodes A1 and A2, and the segment Zk corresponds to a half-wave length portion between the mutually neighboring vibration anti-nodes Ak and Ak+1. Moreover, in each of the segments Zm, the half-wave length portion has a symmetric shape in the longitudinal direction with respect to the vibration node (corresponding Nm) between the two corresponding vibration anti-nodes (corresponding Am and Am+1) as the center. For example, in the segment Z1, the half-wave length portion is symmetric in the longitudinal direction with respect to the vibration node N1 between the vibration anti-nodes A1 and A2 as the center. In the segment Zk, the half-wave length portion is symmetric in the longitudinal direction with respect to the vibration node Nk between the vibration anti-nodes Ak and Ak+1 as the center. Furthermore, each of the segments Zm has a dimension (corresponding Lm) in the longitudinal direction of the half-wave length portion between the two corresponding vibration anti-nodes (corresponding Am and Am+1).

The segments Zm include a plurality of recess segments Zam. In each of the recess segments Zam, a groove (corresponding Vm), which is recessed toward the inner peripheral side, is formed in the half-wave length portion between the corresponding vibration anti-nodes (corresponding Am and Am+1). In FIG. 3, each of the segments Z1, Z3 and Zk is one of the recess segments Zam. In each of the recess segments Zam, the groove (corresponding Vm) is formed over the entire circumference around the longitudinal axis C. In the state in which the vibrating body unit 10 (vibration transmitting member 16) vibrates at the predetermined resonance frequency, in each of the recess segments Zam, the vibration node (corresponding Nm) between the corresponding vibration anti-nodes (corresponding Am and Am+1) is located in the groove (corresponding Vm). For example, in the recess segment Za1, the vibration node N1 is located in the groove V1. In the recess segment Zak, the vibration node Nk is located in the groove Vk. In each of the recess segments Zam, the vibration node (corresponding Nm) is located at a substantially central position of the groove (corresponding Vm) in the longitudinal direction. Accordingly, each of the recess segments Zam has a symmetrical shape in the longitudinal direction with respect to the groove (corresponding Vm) as the center.

It should suffice if two or more of the segments Zm are recess segments Zam. In one example, all segments Zm are recess segments Zam. In another example, at least two of the segments Zm are recess segments Zam, and the segments Zm other than the recess segments Zam are uniform segments Zbm. In this case, in each of the uniform segments Zbm, no groove is formed in the half-wave length portion between the vibration anti-nodes (corresponding Am and Am+1), and the cross-sectional area substantially perpendicular to the longitudinal direction (longitudinal axis C) becomes substantially uniform at Seq from the proximal end to distal end in the half-wave length portion.

Each of the recess segments Zam includes a proximal-side extension (corresponding Xm), a distal-side extension (corresponding Ym) and an intermediate extension (corresponding Mm). In each of the recess segments Zam, the proximal-side extension (corresponding Xm) extends in the longitudinal direction from the proximal end of the half-wave length portion between the two corresponding vibration anti-nodes (corresponding Am and Am+1) to the proximal end of the groove (corresponding Vm), and the distal-side extension (corresponding Ym) extends in the longitudinal direction from the distal end of the groove (corresponding Vm) to the distal end of the half-wave length portion. In addition, in each of the recess segments Zam, the intermediate extension (corresponding Mm) is continuous between the proximal-side extension (corresponding Xm) and distal-side extension (corresponding Ym) in the longitudinal direction, and extends from the proximal end of the groove (corresponding Vm) to the distal end of the groove (corresponding Vm) in the longitudinal direction. For example, in the recess segment Za1, a proximal-side extension X1 extends from the vibration anti-node A1, which is the proximal end of the half-wave length portion, to the proximal end of the groove V1, and a distal-side extension Y1 extends from the distal end of the groove V1 to the vibration anti-node A2 which is the distal end of the half-wave length portion. In addition, an intermediate extension M1 is continuous between the proximal-side extension X1 and the proximal-side extension Y1.

Each of the recess segments Zam is symmetric in the longitudinal direction with respect to the groove (corresponding Vm) as the center. Thus, in each of the recess segments Zam, the dimension in the longitudinal direction of the proximal-side extension (corresponding Xm) is substantially identical to the dimension in the longitudinal direction of the distal-side extension (corresponding Ym). In addition, in each of the recess segments Zam, the cross-sectional area substantially perpendicular to the longitudinal axis C of the proximal-side extension (corresponding Xm) and the cross-sectional area substantially perpendicular to the longitudinal axis C of the distal-side extension (corresponding Ym) are substantially identical to each other. Besides, in each of the recess segments Zam, the cross-sectional area substantially perpendicular to the longitudinal direction becomes substantially uniform at Seq from the proximal end to distal end in the longitudinal direction in each of the proximal-side extension (corresponding Xm) and distal-side extension (corresponding Ym). Accordingly, in this embodiment, all proximal-side extensions Xm, all distal-side extensions Ym and all uniform segments Zbm have a mutually substantially identical cross-sectional area of Seq which is substantially perpendicular to the longitudinal direction. Specifically, in the part between the proximal end of the segment (most proximally located segment) Z1 and the distal end of the segment. (most distally located segment) Zk in the longitudinal direction, the cross-sectional area substantially perpendicular to the longitudinal direction is Seq and substantially uniform except for the grooves Vm (intermediate extensions Mm).

In each of the recess segments Zam, since the groove (corresponding Vm) is formed, the cross-sectional area (corresponding Sm) substantially perpendicular to the longitudinal direction of the intermediate extension (corresponding Mm) is smaller than the cross-sectional area Seq substantially perpendicular to the longitudinal direction of each of the proximal-side extension (corresponding Xm) and distal-side extension (corresponding Ym). In addition, in this embodiment, in each of the recess segments Zam, the dimension (corresponding Wm) in the longitudinal direction of the intermediate extension is less than the dimension in the longitudinal direction of each of the proximal-side extension (corresponding Xm) and distal-side extension (corresponding Ym).

In addition, in the present embodiment, in the recess segment Za1 (segment Z1), an annular liner member 55 is attached to the intermediate extension M1. The liner member 55 is formed of an elastic material such as rubber, and is engaged with the groove V1. The liner member 55 abuts on the intermediate extension M1 from the outer peripheral side in a range from the proximal end of the groove V1 to the distal end of the groove V1 in the longitudinal direction, and abuts on the intermediate extension M1 in the groove V1 over the entire circumference around the longitudinal axis C. Besides, the shaft portion 7 abuts on the liner member 55 from the outer peripheral side. In the state in which the vibrating body unit 10 vibrates at the predetermined resonance frequency, the vibration node N1 is located in the groove V1. Thus, the transmission of ultrasonic vibration from the vibration transmitting member 16 to the shaft portion 7 through the liner member 55 is prevented. The shaft portion 7 supports the vibration transmitting member 16 via the liner members 45, 52 and 55, and maintains the state in which the shaft portion 7 and vibration transmitting member 16 are out of contact.

Besides, at least two of the recess segments Zam are different from each other with respect to at least one of the dimension (corresponding Vm) in the longitudinal direction of the groove (corresponding Vm) and the depth of the groove (corresponding Vm). Thus, at least two of the recess segments Zam are different from each other according to at least one of the dimension (corresponding Wm) in the longitudinal direction of the intermediate extension (corresponding Mm) and the cross-sectional area (corresponding Sm) substantially perpendicular to the longitudinal direction of the intermediate extension (corresponding Mm).

The recess segment Zam is different from the uniform segment Zbm which is not provided with the groove, according to the dimension Lm in the longitudinal direction of the half-wave length portion. Compared to the uniform segment Zbm, the recess segment Zam has a small (short) dimension Lm in the longitudinal direction of the half-wave length portion. In addition, among the recess segments Zam, too, if recess segments Zam are different from each other with respect to at least one of the dimension Wm in the longitudinal direction of the intermediate extension Mm and the cross-sectional area Sm substantially perpendicular to the longitudinal direction of the intermediate extension Mm, the recess segments Zam are different from each other according to the dimension Lm in the longitudinal direction of the half-wave length portion. In fact, among the recess segments Zam, as the dimension Wm in the longitudinal direction of the intermediate extension Mm (groove Vm) is greater, the dimension Lm in the longitudinal direction of the half-wave length portion is smaller (shorter). In addition, among the recess segments Zam, as the cross-sectional area Sm substantially perpendicular to the longitudinal direction of the intermediate extension Mm is smaller (as the depth of the groove Vm is greater), the dimension Lm in the longitudinal direction of the half-wave length portion is smaller (shorter).

In one example, the cross-sectional area Sm substantially perpendicular to the longitudinal direction of the intermediate extension Mm is substantially identical in all recess segments Zam, and the dimensions (W1, W2, Wk) in the longitudinal direction of the intermediate extensions (M1, M2, Mk) are different between at least the recess segments Za1, Za2 and Zak. In addition, the relationship of W2<Wk<W1 is established. In another example, the dimension Wm in the longitudinal direction of the intermediate extension Mm is substantially identical in all recess segments Zam, and the cross-sectional areas (S1, S2, Sk) substantially perpendicular to the longitudinal direction of the intermediate extensions (M1, M2, Mk) are different between at least the recess segments Za1, Za2 and Zak. In addition, the relationship of S2>Sk>S1 is established. In each of these examples, the dimensions (L1, L2, Lk) in the longitudinal direction of the half-wave length portions are different between at least the recess segments Za1, Za2 and Zak, and the relationship of L2>Lk>L1 is established.

As described above, in the present embodiment, as in the above-described examples, the dimensions (corresponding Lm) in the longitudinal direction of the half-wave length portion is different between at least two of the recess segments Zam. Accordingly, in the present embodiment, at least two of the segments Zm (recess segments Zam and uniform segments Zbm) are different with respect to the dimension (corresponding Lm) in the longitudinal direction of the half-wave length portion between the corresponding vibration anti-nodes (corresponding Am and Am+1).

In the recess segment Za1 in which the liner member 55 is engaged with the groove V1, the dimension W1 in the longitudinal direction of the intermediate extension M1 is a predetermined length Wref, and the cross-sectional area S1 substantially perpendicular to the longitudinal direction of the intermediate section M1 is a predetermined cross-sectional area Sref. The predetermined length Wref and the predetermined cross-sectional area Sref are preset values regardless of the physicality such as Young's modulus E of the material of which the vibration transmitting member 16 is formed. Specifically, the predetermined length Wref and predetermined cross-sectional area Sref do not change in accordance with the physical property of the material which forms the vibration transmitting member 16. In one example, the predetermined length Wref is 3.4 mm.

Although the liner member 55 is attached to only the recess segment Za1, the configuration is not limited to this. In one example, the liner member (55) is attached to any one of or to each of any two or more of the recess segments Zam, and the liner member (55) is not attached to all of the other recess segments (corresponding Zam). In this case, too, in each of the recess segments (corresponding Zam) to which the liner members (55) are attached, the dimension (corresponding Wm) in the longitudinal direction of the intermediate extension (corresponding Mm) is the predetermined length Wref, and the cross-sectional area (corresponding Sm) substantially perpendicular to the longitudinal direction of the intermediate section (corresponding Mm) is the predetermined cross-sectional area Sref.

In addition, at least one of the recess segments (corresponding Zam), to which the liner members 55 are not attached, is different from the recess segment (corresponding Zam) to which the liner member 55 is attached, according to at least one of the dimension Wm in the longitudinal direction of the intermediate extension Mm and the cross-sectional area Sm substantially perpendicular to the longitudinal direction of the intermediate extension Mm. Accordingly, in any one of or in each of any two or more of recess segments (corresponding Zam) to which the liner member 55 is not attached, at least one of two cases is applied: one case in which the dimension (corresponding Wm) is different from the predetermined length Wref, and the other case in which the cross-sectional area (corresponding Sm) is different from the predetermined cross-sectional area Sref. In one example, the liner member 55 is attached to only the recess segment Za1, and, in each of the recess segments Za2 and Zak, the dimension (corresponding one of W2 and Wk) is different from the predetermined length Wref corresponding to the dimension W1 of the recess segment Za1. In another example, the liner member 55 is attached to only the recess segment Za1, and, in each of the recess segments Za2 and Zak, the cross-sectional area (corresponding one of S2 and Sk) is different from the predetermined cross-sectional area Sref corresponding to the cross-sectional area S1 of the recess segment Za1.

Additionally, the uniform segment (corresponding Zbm) with no groove or the recess segment (corresponding Zam)

with the least dimension Wm among the recess segments Zam is continuous, on at least one side in the longitudinal direction, with the recess segment (corresponding Zam) with the greatest dimension Wm in the longitudinal direction of the intermediate extension Mm among the recess segments Zam. In one example, the recess segment Za1 has the greatest dimension Wm among the recess segments Zam, and the uniform segment Zb2 or the recess segment Za2, which has the least dimension Wm among the recess segments Zam, is continuous with the distal side (one side in the longitudinal direction) of the recess segment Za1.

Additionally, the uniform segment (corresponding Zbm) with no groove or the recess segment (corresponding Zam) with the greatest cross-sectional area Sm among the recess segments Zam is continuous, on at least one side in the longitudinal direction, with the recess segment (corresponding Zam) with the least cross-sectional area Sm substantially perpendicular to the longitudinal direction of the intermediate extension Mm among the recess segments Zam. In one example, the recess segment Za1 has the smallest cross-sectional area Sm among the recess segments Zam, and the uniform segment Zb2 or the recess segment Za2, which has the greatest cross-sectional area Sm among the recess segments Zam, is continuous with the distal side (one side in the longitudinal direction) of the recess segment Za1.

Next, a manufacturing method of the vibration transmitting member 16 will be described. Here, in the manufacture of the vibration transmitting member 16, there is a case in which the lot of the manufacturer varies from member to member. If the lot of the manufacturer varies from member to member, the physicality such as Young's modulus E varies. Thus, in the manufacture of the vibration transmitting member 16, the physicality including Young's modulus E of the material, of which the vibration transmitting member 16 is formed, is first specified.

Then, based on the physical property such as Young's modulus E, the positions of the vibration anti-node Ai and vibration node Nj in the state in which the vibrating body unit 10 (vibration transmitting member 16) vibrates at the predetermined resonance frequency are specified (determined). Further, each of the segments Zm is formed in a half-wave length portion between two mutually neighboring, corresponding vibration anti-nodes (corresponding Am and Am+1). At this time, the segments Zm are formed in mutually different regions in the longitudinal direction, and each of the segments Zm is formed symmetric in the longitudinal direction with respect to the vibration node (corresponding Nm) between the corresponding vibration anti-nodes (corresponding Am and Am+1) as the center.

Then, with respect to each of the segments Zm, it is determined, based on the physicality such as Young's modulus E, whether each segment Zm is formed as the recess segment (corresponding Zam), or formed as the uniform segment (corresponding Zbm) in which the groove is not formed. Thereby, a plurality of the segments Zm are formed as the recess segments Zam, and the segments Zm other than the recess segments Zam are formed as uniform segments Zbm. In each of the recess segments Zam, the groove (corresponding Vm) is formed in the half-wave length portion in the state in which the vibration node (corresponding Nm) between the vibration anti-nodes (corresponding Am and Am+1) is located in the groove (corresponding Vm).

Then, in each of the recess segments Zam, the proximal-side extension (corresponding Xm), distal-side extension (corresponding Ym) and intermediate extension (corresponding Mm) are formed. At this time, in each of the recess segments Zam, the dimension in the longitudinal direction of the proximal-side extension (corresponding Xm) is made identical to the dimension in the longitudinal direction of the distal-side extension (corresponding Ym), and the cross-sectional area substantially perpendicular to the longitudinal direction of the proximal-side extension (corresponding Xm) is made identical to the cross-sectional area substantially perpendicular to the longitudinal direction of the distal-side extension (corresponding Ym). Besides, in each of the recess segments Zam, the cross-sectional area (corresponding Sm) perpendicular to the longitudinal direction of the intermediate extension (corresponding Mm) is made less than the cross-sectional area perpendicular to the longitudinal direction of each of the proximal-side extension (corresponding Xm) and distal-side extension (corresponding Ym).

In addition, in the manufacture of the vibration transmitting member 16, the liner member (55) is formed. In any one of or in each of any two or more of the recess segments Zam, the liner member (55) is engaged with the groove (corresponding Vm), and the liner member (55) is attached to the intermediate extension (corresponding Mm). When the recess segments Zam are formed, in each of the recess segments (corresponding Zam) to which the liner members (55) are attached, the dimension (corresponding Wm) in the longitudinal direction of the intermediate extension (corresponding Mm) is set to the predetermined length Wref, and the cross-sectional area (corresponding to Sm) substantially perpendicular to the longitudinal direction of the intermediate extension (corresponding Mm) is set to the predetermined cross-sectional area Sref. At this time, regardless of the physicality such as Young's modulus E of the vibration transmitting member 16, in each of the recess segments (corresponding Zam) to which the liner members (55) are attached, the dimension (corresponding Wm) is set to the predetermined length Wref, and the cross-sectional area (corresponding Sm) is set to the predetermined cross-sectional area Sref.

Further, at least one is selected from among the recess segments (corresponding Zam) to which the liner member (55) is not attached. Then, in one selected recess segment (corresponding Zam) or in each of plural selected recess segments (corresponding Zam), at least one of the dimension (corresponding Wm) in the longitudinal direction of the intermediate extension (corresponding Mm) and the cross-sectional area (corresponding Sm) substantially perpendicular to the longitudinal direction of the intermediate extension (corresponding Mm) is adjusted based on the physicality such as Young's modulus E.

Figure 4:
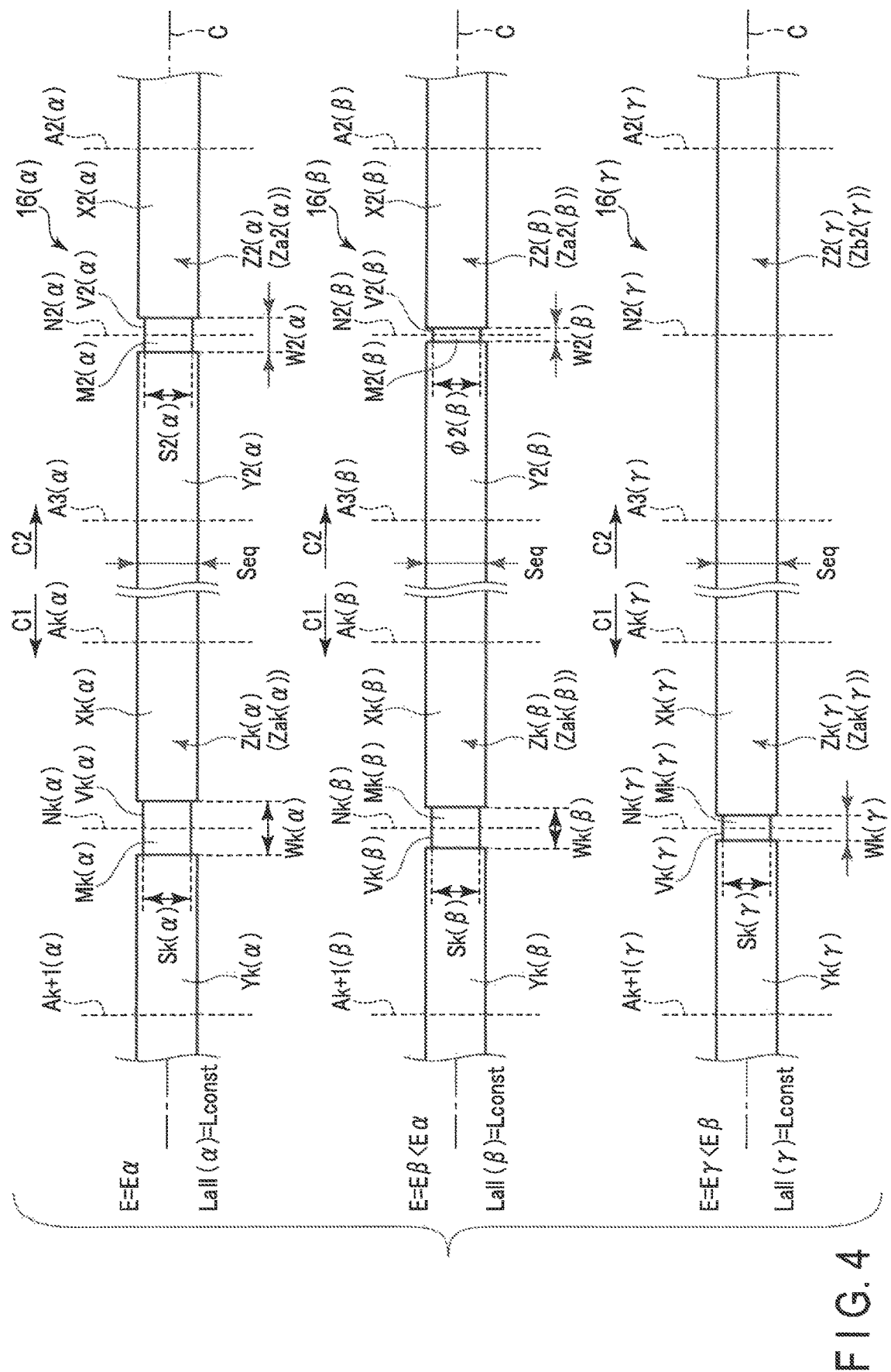
FIG. 4 is a schematic view for describing the decision as to whether each of segments according to the first embodiment is formed as a recess segment or not, and the adjustment of at least one of a dimension and a cross-sectional area of an intermediate extension in any one of recess segments or in each of any two or more of recess segments.

FIG. 4 is a view for describing the decision as to whether each of the segments Zm is formed as the recess segment (corresponding Zam) or not, and the adjustment of at least one of the dimension (corresponding Wm) and cross-sectional area (corresponding Sm) of the intermediate extension (corresponding Mm) in any one recess segment (corresponding Zam) or in each of any two or more recess segments (corresponding Zam). As illustrated in FIG. 4, in the vibration transmitting member 16, there is a case in which the Young's modulus E varies among members, such as Eα, Eβ and Eγ (Eα>Eβ>Eγ). Here, as regards the vibration transmitting member 16(α) which is formed of a material of Young's modulus Eα, the related parts, etc. are indicated by reference numerals and (α). Similarly, the parts, etc. relating to the vibration transmitting member 16(β) which is formed of a material of Young's modulus Eβ are indicated by reference numerals and (α), and the parts, etc. relating to the vibration transmitting member $16(\gamma)$ which is formed of a material of Young's modulus E$\gamma$ are indicated by reference numerals and $(\gamma)$.

In an example illustrated in FIG. 4, in all vibration transmitting members 16 (i.e. regardless of the physicality such as Young's modulus E), the liner member 55 is attached to only the recess segment Za1. Thus, in each vibration transmitting member 16, the dimension W1 of the intermediate extension M1 is set to the predetermined length Wref, and the cross-sectional area S1 of the intermediate extension M1 is set to the predetermined cross-sectional area Sref. In this example, in accordance with the physicality such as Young's modulus E, at least the dimension Wk in the longitudinal direction of the intermediate extension Mk of the recess segment Zak is adjusted. Note that, in this example, in each vibration transmitting member 16, the cross-sectional area Sk substantially perpendicular to the longitudinal direction of the intermediate extension Mk of the recess segment Zak is substantially identical, and the adjustment of the cross-sectional area Sk in accordance with the physicality is not performed. In addition, in this example, in accordance with the physicality such as Young's modulus E, as regards at least the segment Z2, it is determined whether the segment Z2 is formed as the recess segment Za2 or formed as the uniform segment Zb2. In addition, when the segment Z2 is formed as the recess segment Za2, the dimension W2 in the longitudinal direction of the intermediate extension M2 of the recess segment Za2 is adjusted in accordance with the physicality. Note that, in this example, in each of the vibration transmitting members 16 in which the segment Z2 is formed as the recess segment Za2, the cross-sectional area S2 substantially perpendicular to the longitudinal direction of the intermediate extension M2 of the recess segment Za2 is substantially identical, and the adjustment of the cross-sectional area S2 in accordance with the physicality is not performed.

Here, for example, it is assumed that segments Zm, which are made of materials having mutually identical physicality such as Young's modulus E, are formed. When the physicality is identical, in each of the segments Zm, the dimension (corresponding Lm) in the longitudinal direction of the half-wave length portion becomes shorter as the dimension in the longitudinal direction of the groove (corresponding Vm) is greater. On the other hand, in each of the segments Zm, the dimension in the longitudinal direction of the half-wave length portion (corresponding Lm) becomes greater as the dimension in the longitudinal direction of the groove (corresponding Vm) is smaller. When the groove does not exist, the dimension (Lm) in the longitudinal direction of the half-wave length portion becomes greatest.

In this example, the dimension Wk($\beta$) in the recess segment Zak($\beta$) of the vibration transmitting member $16(\beta)$ having a Young's modulus E of E$\beta$ which is less than E$\alpha$ is set to be smaller than the dimension Wk($\alpha$) in the recess segment Zak($\alpha$) of the vibration transmitting member $16(\alpha)$ having the Young's modulus E that is E$\alpha$. In addition, the dimension W2($\beta$) in the recess segment Za2($\beta$) of the vibration transmitting member $16(\beta)$ is set to be smaller than the dimension W2($\alpha$) in the recess segment Za2($\alpha$) of the vibration transmitting member $16(\alpha)$. Thereby, in the vibration transmitting members $16(\alpha)$ and $16(\beta)$, the influence of the variance of the Young's modulus E therebetween upon the resonance frequency and a total length La11 in the longitudinal direction is canceled by the adjustment of the dimensions W2 and Wk. Accordingly, in the vibration transmitting members $16(\alpha)$ and $16(1)$, the resonance frequencies are adjusted to be identical to each other, and the total lengths La11 in the longitudinal direction are also adjusted to be identical to each other. Specifically, each of the vibration transmitting members $16(\alpha)$ and $16(\alpha)$ vibrates at a predetermined resonance frequency (e.g. 47 kHz) in a state of transmitting ultrasonic vibration, and the total length (La11($\alpha$), La11($\beta$)) in the longitudinal direction becomes a predetermined dimension Lconst. As described above, by disposing the segments Zm with proper lengths along the longitudinal axis C in accordance with the physicality, the resonance frequency is adjusted and the total length La11 of the vibration transmitting member 16 is properly adjusted.

Besides, the dimension Wk($\gamma$) in the recess segment Zak($\gamma$) of the vibration transmitting member $16(\gamma)$ having a Young's modulus E of E$\gamma$ which is less than EP is set to be smaller than the dimension Wk($\beta$) in the recess segment Zak($\gamma$) of the vibration transmitting member $16(\beta)$ having the Young's modulus E that is E$\beta$. In addition, in the vibration transmitting member $16(\gamma)$, the segment Z2($\gamma$) is formed as a uniform segment Zb2($\gamma$). Thereby, in the vibration transmitting members $16(\beta)$ and $16(\gamma)$, the influence of the variance of the Young's modulus E therebetween upon the resonance frequency and the total length La11 in the longitudinal direction is canceled by the adjustment of the dimension Wk and the formation of the segment Z2($\gamma$) as the uniform segment Zb2($\gamma$). Accordingly, in the vibration transmitting members $16(\beta)$ and $16(\gamma)$, the resonance frequencies are adjusted to be identical to each other, and the total lengths La11 in the longitudinal direction are also adjusted to be identical to each other. Specifically, each of the vibration transmitting members $16(\beta)$ and $16(\gamma)$ vibrates at the predetermined resonance frequency (e.g. 47 kHz) in a state of transmitting ultrasonic vibration, and the total length (La11($\gamma$), La11($\gamma$)) in the longitudinal direction becomes the predetermined dimension Lconst.

As described above, in this example, in each of at least one (e.g. Za2, Zak) of the recess segments Zam, the dimension (corresponding Wm) in the longitudinal direction of the intermediate extension (corresponding Mm) is adjusted based on the physical property such as Young's modulus E. In addition, with respect to any one (e.g. Z2) of or each of any two or more of the segments Zm, it is determined, based on the physicality such as Young's modulus E, whether the segment Zm is formed as the recess segment (corresponding Zam) or formed as the uniform segment (corresponding Zbm). Thereby, regardless of the physicality, in all vibration transmitting members 16, the resonance frequency is adjusted to the predetermined resonance frequency, and the total length La11 in the longitudinal direction is set to the predetermined dimension Lconst.

In addition, in this example, by the adjustment of the dimension (corresponding Wm) based on the physicality, any one of or each of any two or more (e.g. Za2, Zak) of the recess segments Zam differs from the recess segment (e.g. Za1), to which the liner member 55 is attached, with respect to the dimension (corresponding Wm) in the longitudinal direction of the intermediate extension (corresponding to Mm). Specifically, in each of at least one (e.g. Za2, Zak) of the recess segments Zam, the dimension (corresponding Wm) in the longitudinal direction of the intermediate extension (corresponding to Mm) is different from the predetermined length Wref. Thereby, in each of the vibration transmitting members 16, at least two (e.g. Za1, Zak; Za1, Za2, Zak) of the recess segments Zam are formed in such a state that the dimensions (corresponding Wm) in the longitudinal direction of the intermediate extensions (corresponding Mm) are different from each other.

In another example, too, in all vibration transmitting members 16 (i.e. regardless of the physicality such as Young's modulus E), the liner member 55 is attached to only the recess segment Za1. However, in this example, at least the cross-sectional area Sk substantially perpendicular to the longitudinal direction of the intermediate extension Mk of the recess segment Zak is adjusted in accordance with the physicality such as Young's modulus E. Note that, in this example, in each of the vibration transmitting members 16, the dimension Wk in the longitudinal direction of the intermediate extension Mk of the recess segment Zak is substantially identical, and the adjustment of the dimension Wk in accordance with the physicality is not performed.

Here, for example, it is assumed that each of the segments Zm, which are made of materials having mutually identical physicality such as Young's modulus E, is formed. When the physicality is identical, in each of the segments Zm, the dimension (corresponding Lm) in the longitudinal direction of the half-wave length portion becomes shorter as the depth of the groove (corresponding Vm) is greater. On the other hand, in each of the segments Zm, the dimension in the longitudinal direction of the half-wave length portion (corresponding Lm) becomes greater as the depth of the groove (corresponding Vm) is smaller. When the groove does not exist, the dimension (Lm) in the longitudinal direction of the half-wave length portion becomes greatest.

In this example, the cross-sectional area $Sk(\beta)$ in the recess segment $Zak(\beta)$ of the vibration transmitting member $16(\beta)$ having the Young's modulus E of E1 which is less than $E\alpha$ is set to be greater than the cross-sectional area $Sk(\alpha)$ in the recess segment $Zak(\alpha)$ of the vibration transmitting member $16(\alpha)$ having the Young's modulus E that is $E\alpha$. Thereby, in the vibration transmitting members $16(\alpha)$ and $16(\beta)$, the influence of the variance of the Young's modulus E therebetween upon the resonance frequency and the total length La11 in the longitudinal direction is canceled by the adjustment of the cross-sectional area Sk. Accordingly, in the vibration transmitting members $16(\alpha)$ and $16(\beta)$, the resonance frequencies are adjusted to be identical to each other, and the total lengths La11 in the longitudinal direction are also adjusted to be identical to each other. Specifically, each of the vibration transmitting members $16(\alpha)$ and $16(\beta)$ vibrates at the predetermined resonance frequency (e.g. 47 kHz) in a state of transmitting ultrasonic vibration, and the total length ($La11(\alpha)$, $La11(\beta)$) in the longitudinal direction becomes the predetermined dimension Lconst.

As described above, in this example, in each of at least one (e.g. Zak) of the recess segments Zam, the cross-sectional area (corresponding Sm) substantially perpendicular to the longitudinal direction of the intermediate extension (corresponding Mm) is adjusted based on the physicality such as Young's modulus E. Thereby, regardless of the physicality, in all vibration transmitting members 16, the resonance frequency is adjusted to the predetermined resonance frequency, and the total length La11 in the longitudinal direction is set to the predetermined dimension Lconst.

In addition, in this example, by the adjustment of the dimension (corresponding Sm) based on the physicality, each of at least one (e.g. Zak) of the recess segments Zam differs from the recess segment (e.g. Za1), to which the liner member 55 is attached, with respect to the cross-sectional area (corresponding Sm) substantially perpendicular to the longitudinal direction of the intermediate extension (corresponding to Mm). Specifically, in any one (e.g. Zak) of or in each of any two or more of the recess segments Zam, the cross-sectional area (corresponding Sm) substantially perpendicular to the longitudinal direction of the intermediate extension (corresponding to Mm) differs from the predetermined cross-sectional area Sref. Thereby, in each of the vibration transmitting members 16, at least two (e.g. Za1, Zak) of the recess segments Zam are formed in such a state that the cross-sectional areas (corresponding Sm) substantially perpendicular to the longitudinal direction of the intermediate extensions (corresponding Mm) are different from each other.

In another example, in any one (e.g. Zak) of or in each of any two or more of the recess segments Zam, the dimension (corresponding Wm) in the longitudinal direction of the intermediate extension (corresponding Mm) and the cross-sectional area (corresponding Sm) substantially perpendicular to the longitudinal direction of the intermediate extension (corresponding Mm) are adjusted based on the physicality such as Young's modulus E. Thereby, regardless of the physicality, in all vibration transmitting members 16, the resonance frequency is adjusted to the predetermined resonance frequency, and the total length La11 in the longitudinal direction is set to the predetermined dimension Lconst.

In addition, in this example, by the adjustment of the dimension (corresponding Wm) and cross-sectional area (corresponding Sm) based on the physicality, each of at least one (e.g. Zak) of the recess segments Zam differs from the recess segment (e.g. Za1), to which the liner member 55 is attached, with respect to the dimension (corresponding Wm) in the longitudinal direction of the intermediate extension (corresponding to Mm) and with respect to the cross-sectional area (corresponding Sm) substantially perpendicular to the longitudinal direction of the intermediate extension (corresponding Mm). Specifically, in any one (e.g. Zak) of or in each of any two or more of the recess segments Zam, the dimension (corresponding Wm) in the longitudinal direction of the intermediate extension (corresponding to Mm) is different from the predetermined length Wref, and the cross-sectional area (corresponding Sm) substantially perpendicular to the longitudinal direction of the intermediate extension (corresponding Mm) is different from the predetermined cross-sectional area Sref. Thereby, in each of the vibration transmitting members 16, at least two (e.g. Za1, Zak) of the recess segments Zam are formed in such a state that the dimensions (corresponding Wm) in the longitudinal direction of the intermediate extensions (corresponding Mm) are different from each other and the cross-sectional areas (corresponding Sm) substantially perpendicular to the longitudinal direction of the intermediate extensions (corresponding Mm) are different from each other.

In the present embodiment including the above-described examples, etc., in each of at least one of the recess segments Zam, the intermediate extension (corresponding Mm), in which at least one of the dimension (corresponding Wm) and cross-sectional area (corresponding Sm) is adjusted based on the physicality, is provided over a range including the vibration node (corresponding Nm) and its vicinity. Specifically, in any one of or in each of any two or more of the recess segments Zam, the dimension (corresponding Wm) and cross-sectional area (corresponding Sm) are adjusted at and near the vibration node (corresponding Nm). In the half-wave length portion of each segment Zm, the stress due to ultrasonic vibration becomes maximum at the vibration node (corresponding Nm) and increases at and near the vibration node (corresponding Nm). Accordingly, in each of at least one of the recess segments Zam, in the region where the stress due to ultrasonic vibration is large, at least one of the dimension (corresponding Wm) and cross-sectional area (corresponding Sm) of the intermediate extension (corresponding Mm) is adjusted based on the physicality. Thus, the influence of the adjustment of at least one of the dimension (corresponding Wm) and cross-sectional area (corresponding Sm) of the intermediate extension (corresponding Mm) in at least one of the recess segments Zam, upon the resonance frequency and the total length La11 in the longitudinal direction of the vibration transmitting member 16, becomes large. Accordingly, the influence of the variance of the physicality such as Young's modulus E, upon the resonance frequency and the total length La11 in the longitudinal direction of the vibration transmitting member 16, is properly canceled by adjusting at least one of the dimension (corresponding Wm) and cross-sectional area (corresponding Sm) of the intermediate extension (corresponding Mm) in at least one of the recess segments Zam.

Besides, in this embodiment, in the manufacture of the vibration transmitting member 16, the uniform segment (corresponding Zbm) with no groove or the recess segment (corresponding Zam) with the least dimension Wm among the recess segments Zam is made continuous, on at least one side in the longitudinal direction, with the recess segment (corresponding Zam) with the greatest dimension Wm in the longitudinal direction of the intermediate extension Mm among the recess segments Zam. Furthermore, the uniform segment (corresponding Zbm) with no groove Vm or the recess segment (corresponding Zam) with the greatest cross-sectional area Sm among the recess segments Zam is made continuous, on at least one side in the longitudinal direction, with the recess segment (corresponding Zam) with the least cross-sectional area Sm substantially perpendicular to the longitudinal direction of the intermediate extension Mm among the recess segments Zam.

Next, the function and advantageous effects of the vibration transmitting member 16 will be described. In the present embodiment, even if the physicality such as Young's modulus E of materials, of which the vibration transmitting members 16 are formed, varies from member to member, the resonance frequency is adjusted to the predetermined resonance frequency in all vibration transmitting members 16. Thus, in the ultrasonic treatment instrument 2 including the vibration transmitting member 16, the transformation ratio, etc. in the horns (e.g. 42, 46, 53) provided in the vibration transmitting member 16 are prevented from varying among products. Thereby, the amplitude and vibration velocity of ultrasonic vibration in the energy applying portion 17 are prevented from varying among products. Therefore, regardless of the physical property such as Young's modulus E, a treated target is stably treated by the energy applying portion 17.

Additionally, in this embodiment, even if the physicality such as Young's modulus E of materials, of which the vibration transmitting members 16 are formed, varies from member to member, the total length La11 in the longitudinal direction is set to the predetermined dimension Lconst in all vibration transmitting members 16. Thereby, in the ultrasonic treatment instrument 2 including the vibration transmitting member 16, the attachment position of the liner member (43, 51, 55) to the vibration transmitting member 16 and the length of projection of the vibration transmitting member 16 from the shaft portion 7 toward the distal side are prevented from varying among products. Specifically, since there is no variance among the total lengths La11 in the longitudinal direction of the vibration transmitting members 16, the influence on the manufacture and treatment performance of the ultrasonic treatment instrument 2 is decreased.

Thereby, the labor, etc. in the manufacture of the ultrasonic treatment instrument 2 are reduced, and the treated target is more stably treated.

Additionally, in each of the recess segments Zam, the half-wave length portion has a symmetric shape in the longitudinal direction with respect to the vibration node (corresponding Nm) (groove (corresponding Vm)) as the center, and the vibration node (corresponding Nm) is located in the groove (corresponding Vm). Hence, in each of the recess segments Zam, the amplitude at the distal end (corresponding Am+1) of the half-wave length portion becomes substantially identical to the amplitude at the proximal end (corresponding Am) of the half-wave length portion. Thus, in this embodiment, the amplitude of ultrasonic vibration at the distal end of the segment (most distally segment) Zk hardly varies relative to the amplitude of ultrasonic vibration at the proximal end of the segment (most proximally segment) Z1. Therefore, even when the groove Vm is provided, the amplitude of ultrasonic vibration is stabilized in the energy applying portion 17.

Additionally, in this embodiment, in each of the recess segments (corresponding Zam) to which the liner members (55) are attached, the dimension (corresponding Wm) in the longitudinal direction of the intermediate extension (corresponding Mm) is the predetermined length Wref, and the cross-sectional area (corresponding Sm) substantially perpendicular to the longitudinal direction of the intermediate extension (corresponding Mm) is the predetermined cross-sectional area Sref. By this configuration, the vibration transmitting member 16 is properly supported by the shaft portion 7 via the liner member (55), and transmission of ultrasonic vibration to the shaft portion 7 through the liner member (55) is more properly prevented.

Additionally, in this embodiment, the uniform segment (corresponding Zbm) with no groove or the recess segment (corresponding Zam) with the smallest dimension Wm among the recess segments Zam is continuous, on at least one side in the longitudinal direction, with the recess segment (corresponding Zam) with the greatest dimension Wm in the longitudinal direction of the intermediate extension Mm among the recess segments Zam. Besides, the uniform segment (corresponding Zbm) or the recess segment (corresponding Zam) with the greatest cross-sectional area Sm among the recess segments Zam is continuous, on at least one side in the longitudinal direction, with the recess segment (corresponding Zam) with the smallest cross-sectional area Sm substantially perpendicular to the longitudinal direction of the intermediate extension Mm among the recess segments Zam. Thereby, even when the groove Vm is provided, the flexural strength in the vibrating state in the vibration transmitting member 16 is prevented from locally decreasing.

(Modifications)

In the above-described embodiment, etc., the handle 12 is located on the distal side with respect to the grip 11, and the handle 12 moves substantially parallel to the longitudinal direction in each of the opening motion and closing motion. However, the configuration is not limited to this. For example, in one modification, the handle 12 may be located on the proximal side with respect to the grip 11. In another modification, the handle 12 may move in a direction crossing the longitudinal direction in each of the opening movement and closing movement. In still another modification, the rotation knob 21 may not be provided.

Additionally, in one modification, the ultrasonic transducer 23 may not be provided with the relay member 25, and the piezoelectric elements 26 and electrode members 27A and 27B may be directly attached to the vibration transmitting member 16. In addition, the positions and number of horns (42, 46, 53) are not limited to those in the above embodiment, etc. For example, in one modification, at least one horn (42, 46, 53) is provided in the vibration transmitting member 16, and each of the horns is located in a region different from the segment Zm in the longitudinal direction in the vibration transmitting member 16. Furthermore, in the state in which the vibration transmitting member 16 vibrates at the predetermined resonance frequency, each of the horns is located apart from each of the vibration anti-nodes Ai in the longitudinal direction.

Additionally, the positions and number of liner members (45, 52), which are attached to the vibration transmitting member 16 in regions different from the segments Zm in the longitudinal direction are not limited to those in the above embodiment, etc. For example, in one modification, at least one liner member (45, 52) is attached to the vibration transmitting member 16 in a region different from the segment Zm in the longitudinal direction. Furthermore, in the state in which the vibration transmitting member 16 vibrates at the predetermined resonance frequency, any one of the vibration nodes Nj is located in each of the liner members. Besides, in addition to the ultrasonic vibration, other treatment energy may be supplied to the end effector 8. For example, in one modification, ultrasonic vibration is transmitted to the energy applying portion 17, and high-frequency electric energy is supplied to the energy applying portion 17 and grasping member 18. In this case, a high-frequency current is passed between the energy applying portion 17 and grasping member 18 through a grasped treated target.

Additionally, in one modification, the end effector 8 may not be provided with the grasping member 18. In this case, none of the grip 11, handle 12 and movable portion 15 is provided, and the energy applying portion 17 has a hook shape, a spatula shape or a curette shape. In this modification, in the state in which the energy applying portion 17 is put in contact with the treated target, ultrasonic vibration is transmitted to the energy applying portion 17 (end effector 8). Then, by applying the transmitted ultrasonic vibration, the treated target is treated by using the ultrasonic vibration. In this case, too, in addition to the ultrasonic vibration, other treatment energy may be supplied to the energy applying portion 17.

In the above-described embodiment, etc., the vibration transmitting member (16) transmits ultrasonic vibration which is generated by the ultrasonic transducer (23), thereby vibrating at a predetermined resonance frequency. The vibration transmitting member (16) includes a plurality of segments (Zm) which extend in mutually different regions in the longitudinal direction. In the state in which the vibration transmitting member (16) vibrates at the predetermined resonance frequency, each of the segments (Zm) corresponds to a half-wave length portion between two mutually neighboring, corresponding vibration anti-nodes (corresponding Am and Am+1). In each of the segments (Zm), the half-wave length portion is symmetric in the longitudinal direction with respect to the vibration node (Nm) between the two corresponding vibration anti-nodes (corresponding Am and Am+1) as the center. The plural segments (Zm) include a plurality of recess segments (Zam). In each of the recess segments (Zam), a groove (corresponding Vm), which is recessed toward the inner peripheral side, is formed in the half-wave length portion, and the vibration node (Nm) between the two corresponding vibration anti-nodes (corresponding Am and Am+1) is located in the groove (Vm).

Each of the recess segments (Zam) includes a proximal-side extension (corresponding Xm) which extends in the longitudinal direction from the proximal end of the half-wave length portion to the proximal end of the groove (corresponding Vm), a distal-side extension (corresponding Ym) which extends in the longitudinal direction from the distal end of the groove (corresponding Vm) to the distal end of the half-wave length portion, and an intermediate extension (corresponding Mm) which extends in the longitudinal direction from the proximal end of the groove (corresponding Vm) to the distal end of the groove (corresponding Vm). In each of the recess segments (Zam), the dimension in the longitudinal direction of the proximal-side extension (corresponding Xm) is identical to the dimension in the longitudinal direction of the distal-side extension (corresponding Ym), and the cross-sectional area perpendicular to the longitudinal direction of the proximal-side extension (corresponding Xm) is identical to the cross-sectional area perpendicular to the longitudinal direction of the distal-side extension (corresponding Ym). In each of the recess segments (Zam), the cross-sectional area (corresponding Sm) perpendicular to the longitudinal direction of the intermediate extension (corresponding Mm) is smaller than the cross-sectional area perpendicular to the longitudinal direction of each of the proximal-side extension (corresponding Xm) and the distal-side extension (corresponding Ym). At least two of the recess segments (Zam) are different from each other with respect to at least one of the dimension (corresponding Wm) in the longitudinal direction of the intermediate extension (corresponding Mm) and the cross-sectional area (corresponding Sm) perpendicular to the longitudinal direction of the intermediate extension (corresponding Mm).

Hereafter, characteristic items will be additionally described.

(Additional Item 1)

A manufacturing method of a vibration transmitting member to which an ultrasonic transducer is attached, and which vibrates at a predetermined resonance frequency by transmitting ultrasonic vibration generated by the ultrasonic transducer, the method comprising:

specifying physicality including a Young's modulus of a material of which the vibration transmitting member is formed;

specifying, based on the physicality, positions of a vibration anti-node and a vibration node in a state in which the vibration transmitting member vibrates at the predetermined resonance frequency;

forming a plurality of segments extending in mutually different regions in a longitudinal direction, each of the segments being formed in a half-wave length portion between two mutually neighboring, corresponding vibration anti-nodes;

forming, in each of the segments, the half-wave length portion symmetrically in the longitudinal direction with respect to a vibration node between the two corresponding vibration anti-nodes as a center;

forming a plurality of recess segments from among the segments, a groove recessed toward an inter peripheral side being formed in the half-wave length portion in each of the recess segments, and the groove being formed such that the vibration node between the two corresponding vibration anti-nodes is located in the groove;

forming, in each of the recess segments, a proximal-side extension from a proximal end of the half-wave length portion to a proximal end of the groove in the longitudinal direction, a distal-side extension from a distal end of the groove to a distal end of the half-wave length portion in the longitudinal direction, and an intermediate extension from the proximal end of the groove to the distal end of the groove in the longitudinal direction;

setting, in each of the recess segments, a dimension in the longitudinal direction of the proximal-side extension to be identical to a dimension in the longitudinal direction of the distal-side extension, and setting a cross-sectional area perpendicular to the longitudinal direction of the proximal-side extension to be identical to a cross-sectional area perpendicular to the longitudinal direction of the distal-side extension;

setting, in each of the recess segments, a cross-sectional area perpendicular to the longitudinal direction of the intermediate extension to be less than the cross-sectional area perpendicular to the longitudinal direction of each of the proximal-side extension and the distal-side extension; and adjusting, based on the physicality, in each of at least one of the recess segments, at least one of a dimension in the longitudinal direction of the intermediate extension and the cross-sectional area perpendicular to the longitudinal direction of the intermediate extension, thereby adjusting a total length in the longitudinal direction of the vibration transmitting member to a predetermined dimension, and adjusting a resonance frequency of the vibration transmitting member to the predetermined resonance frequency.

(Additional Item 2)

The manufacturing method of additional item 1, further comprising:

forming a liner member of an elastic material; and abutting the liner member on the intermediate extension from an outer peripheral side, and engaging the liner member with the groove, in any one of or in each of any two or more of the recess segments.

(Additional Item 3)

The manufacturing method of additional item 2, further comprising:

setting, in each of the recess segment/segments in which the liner member/members is/are engaged with the grooves, the dimension in the longitudinal direction of the intermediate extension to a predetermined length, and setting the cross-sectional area perpendicular to the longitudinal direction of the intermediate extension to a predetermined cross-sectional area.

(Additional Item 4)

The manufacturing method of additional item 3, further comprising:

selecting, from among the recess segment/segments to which the liner member is not attached, the at least one recess segment in which at least one of the dimension in the longitudinal direction of the intermediate extension and the cross-sectional area perpendicular to the longitudinal direction of the intermediate extension is adjusted.

(Additional Item 5)

The manufacturing method of additional item 4, further comprising:

performing at least either of:

setting, in each of the selected recess segment/segments, the dimension in the longitudinal direction of the intermediate extension to be different from the predetermined length; and setting, in each of the selected recess segment/segments, the cross-sectional area perpendicular to the longitudinal direction of the intermediate extension to be different from the predetermined cross-sectional area.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration transmitting member comprising:
an attached portion to which an ultrasonic transducer is attached, the ultrasonic transducer being configured to vibrate the vibration transmitting member at a predetermined resonance frequency by transmitting ultrasonic vibration; and
a plurality of segments which are disposed in a longitudinal direction, wherein
each of the segments has a dimension of a half-wave length between mutually neighboring vibration anti-nodes and sets a vibration node as a center, in a state in which the vibration transmitting member vibrates at the predetermined resonance frequency,
at least two of the segments are recess segments, each of the recess segments being configured such that a groove recessed toward an inter peripheral side is formed in a portion in which the vibration node is located,
each of the recess segments includes a proximal-side extension extending from a proximal end of the half-wave length to a proximal end of the groove in the longitudinal direction, a distal-side extension extending from a distal end of the groove to a distal end of the half-wave length in the longitudinal direction, and an intermediate extension extending from the proximal end of the groove to the distal end of the groove in the longitudinal direction,
the proximal-side extension and the distal-side extension, in each of the recess segments, have an identical dimension in the longitudinal direction and an identical cross-sectional area perpendicular to the longitudinal direction relative to each other,
at least two of the recess segments are different from each other with respect to at least one of a dimension in the longitudinal direction of the intermediate extension and a cross-sectional area perpendicular to the longitudinal direction of the intermediate extension, and
the segments include a uniform segment having a uniform cross-sectional area perpendicular to the longitudinal direction over a length of the half-wave length.

2. The vibration transmitting member of claim 1, further comprising a liner member which is formed of an elastic material, the liner member being engaged with the groove in a state in which the liner member abuts on the intermediate extension from an outer peripheral side in any one of or in each of any two or more of the recess segments.

3. The vibration transmitting member of claim 1, wherein the cross-sectional area perpendicular to the longitudinal direction of the uniform segment is identical to the cross-sectional area perpendicular to the longitudinal direction of each of the proximal-side extension and the distal-side extension in each of the recess segments.

4. The vibration transmitting member of claim 1, wherein the segments include a segment provided with a horn.

5. The vibration transmitting member of claim 1, wherein a vibration anti-node is located at a distal end of the vibration transmitting member in a state in which the vibration transmitting member is vibrated at the predetermined resonance frequency.

6. An ultrasonic treatment instrument comprising:
the vibration transmitting member of claim 1; and
a housing which is capable of being held, and which is configured such that the vibration transmitting member extends from an inside of the housing toward a distal side, the ultrasonic transducer being attached to the vibration transmitting member in the inside of the housing.

7. The ultrasonic treatment instrument of claim 6, further comprising a shaft coupled to the housing from the distal side, the vibration transmitting member extending through an inside of the shaft.

8. The ultrasonic treatment instrument of claim 7, further comprising a liner member formed of an elastic material, the liner member being engaged with the groove in a state of abutting on the intermediate extension from an outer peripheral side, in any one of or in each of any two or of the recess segments,
wherein the shaft is configured to abut on the liner member from the outer peripheral side, and configured to support the vibration transmitting member via the liner member in a state in which the vibration transmitting member and the shaft are out of contact.

9. A vibration transmitting member comprising:
an attached portion to which an ultrasonic transducer is attached, the ultrasonic transducer being configured to vibrate the vibration transmitting member at a predetermined resonance frequency by transmitting ultrasonic vibration; and
a plurality of segments which are disposed in a longitudinal direction, wherein
each of the segments has a dimension of a half-wave length between mutually neighboring vibration anti-nodes and sets a vibration node as a center, in a state in which the vibration transmitting member vibrates at the predetermined resonance frequency,
at least two of the segments are recess segments, each of the recess segments being configured such that a groove recessed toward an inter peripheral side is formed in a portion in which the vibration node is located,
each of the recess segments includes a proximal-side extension extending from a proximal end of the half-wave length to a proximal end of the groove in the longitudinal direction, a distal-side extension extending from a distal end of the groove to a distal end of the half-wave length in the longitudinal direction, and an intermediate extension extending from the proximal end of the groove to the distal end of the groove in the longitudinal direction,
the proximal-side extension and the distal-side extension, in each of the recess segments, have an identical dimension in the longitudinal direction and an identical cross-sectional area perpendicular to the longitudinal direction relative to each other,
at least two of the recess segments are different from each other with respect to at least one of a dimension in the longitudinal direction of the intermediate extension and a cross-sectional area perpendicular to the longitudinal direction of the intermediate extension, and
a vibration anti-node is located at a distal end of the vibration transmitting member in a state in which the vibration transmitting member is vibrated at the predetermined resonance frequency.

10. The vibration transmitting member of claim 9, further comprising a liner member which is formed of an elastic material, the liner member being engaged with the groove in a state in which the liner member abuts on the intermediate extension from an outer peripheral side in any one of or in each of any two or more of the recess segments.

11. The vibration transmitting member of claim 9, wherein the segments include a segment provided with a horn.

12. An ultrasonic treatment instrument comprising:
the vibration transmitting member of claim 9; and
a housing which is capable of being held, and which is configured such that the vibration transmitting member extends from an inside of the housing toward a distal side, the ultrasonic transducer being attached to the vibration transmitting member in the inside of the housing.

13. The ultrasonic treatment instrument of claim 12, further comprising a shaft coupled to the housing from the distal side, the vibration transmitting member extending through an inside of the shaft.

14. The ultrasonic treatment instrument of claim 13, further comprising a liner member formed of an elastic material, the liner member being engaged with the groove in a state of abutting on the intermediate extension from an outer peripheral side, in any one of or in each of any two or of the recess segments,
wherein the shaft is configured to abut on the liner member from the outer peripheral side, and configured to support the vibration transmitting member via the liner member in a state in which the vibration transmitting member and the shaft are out of contact.

* * * * *